US011607279B2

(12) United States Patent
Chaplin

(10) Patent No.: US 11,607,279 B2
(45) Date of Patent: Mar. 21, 2023

(54) INSTRUMENT INTERFACE FOR ROBOTIC SURGICAL INSTRUMENT

(71) Applicant: CMR Surgical Limited, Cambridge (GB)

(72) Inventor: Ben Robert Chaplin, Cambridgeshire (GB)

(73) Assignee: CMR Surgical Limited, Cambridge (GB)

( * ) Notice: Subject to any disclaimer, the term of this patent is extended or adjusted under 35 U.S.C. 154(b) by 409 days.

(21) Appl. No.: 16/620,327

(22) PCT Filed: Jun. 6, 2018

(86) PCT No.: PCT/GB2018/051543
§ 371 (c)(1),
(2) Date: Dec. 6, 2019

(87) PCT Pub. No.: WO2018/224826
PCT Pub. Date: Dec. 13, 2018

(65) Prior Publication Data
US 2020/0197109 A1 Jun. 25, 2020

(30) Foreign Application Priority Data

Jun. 6, 2017 (GB) .................................... 1709016
Jun. 6, 2017 (GB) .................................... 1709017
Aug. 24, 2017 (GB) .................................... 1713625

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/29* (2013.01); *A61B 34/71* (2016.02); *B25J 9/0009* (2013.01);
(Continued)

(58) Field of Classification Search
CPC ......... A61B 34/30; A61B 17/29; A61B 34/71; A61B 2017/2927; A61B 2017/2932;
(Continued)

(56) References Cited

U.S. PATENT DOCUMENTS 5,807,378 A 9/1998 Jensen et al.
6,394,998 B1 5/2002 Wallace et al.
(Continued)

FOREIGN PATENT DOCUMENTS

CN 205514900 8/2016
EP 2783643 B1 1/2019
(Continued)

OTHER PUBLICATIONS

Examination Report dated May 17, 2021, for related Indian Patent Application No. 201927047874.
(Continued)

*Primary Examiner* — Richard G Louis
(74) *Attorney, Agent, or Firm* — Renner, Otto, Boisselle & Sklar, LLP

(57) ABSTRACT

A robotic surgical instrument, comprising: a shaft; an end effector element; an articulation at a distal end of the shaft for articulating the end effector element, the articulation comprising: a first and second joint permitting the end effector element to adopt a range of configurations relative to a longitudinal axis of the shaft, the first joint being driveable by a first pair of driving elements having a first positional accuracy requirement and the second joint being driveable by a second pair of driving elements having a second positional accuracy requirement lower than the positional accuracy requirement of the first pair of driving elements; and an instrument interface at a proximal end of the shaft, comprising: a chassis formed from the attachment of a first chassis portion to a second chassis portion, the first
(Continued)

chassis portion comprising a mounting surface to which the shaft is mounted; wherein the first pair of driving elements are secured relative to the first chassis portion.

20 Claims, 12 Drawing Sheets

(51) Int. Cl.
  *A61B 17/29* (2006.01)
  *B25J 9/10* (2006.01)
  *B25J 15/00* (2006.01)
  *B25J 17/02* (2006.01)
  *B25J 9/00* (2006.01)
  *A61B 17/00* (2006.01)

(52) U.S. Cl.
  CPC ............. *B25J 9/104* (2013.01); *B25J 9/1045* (2013.01); *B25J 15/0028* (2013.01); *B25J 17/02* (2013.01); *B25J 17/0283* (2013.01); *A61B 2017/00477* (2013.01); *A61B 2017/2927* (2013.01); *A61B 2017/2929* (2013.01); *A61B 2017/2932* (2013.01); *A61B 2017/2938* (2013.01); *A61B 2034/302* (2016.02); *A61B 2034/305* (2016.02); *A61B 2034/306* (2016.02); *A61B 2034/715* (2016.02)

(58) Field of Classification Search
  CPC .... A61B 2034/306; A61B 2017/00477; A61B 2017/2929; A61B 2017/2938; A61B 2034/302; A61B 2034/305; A61B 2034/715; B25J 9/0009; B25J 17/02; B25J 9/104; B25J 9/1045; B25J 15/0028; B25J 17/0283
  See application file for complete search history.

(56) References Cited

U.S. PATENT DOCUMENTS

| | | | |
|---|---|---|---|
| 7,169,141 | B2 | 1/2007 | Brock et al. |
| 2002/0128633 | A1 | 9/2002 | Brock et al. |
| 2006/0016136 | A1 | 1/2006 | Moller, Jr. |
| 2008/0046122 | A1* | 2/2008 | Manzo .................. A61B 34/71 700/245 |
| 2009/0247943 | A1* | 10/2009 | Kirschenman ......... A61B 34/71 604/95.04 |
| 2010/0170519 | A1 | 7/2010 | Romo et al. |
| 2011/0130718 | A1 | 6/2011 | Kidd et al. |
| 2013/0317519 | A1 | 11/2013 | Romo et al. |
| 2014/0276942 | A1 | 9/2014 | Kirschenman et al. |
| 2015/0257841 | A1 | 9/2015 | Dach, II |
| 2015/0265355 | A1* | 9/2015 | Prestel .................. A61B 34/30 606/130 |
| 2017/0027656 | A1 | 2/2017 | Robert et al. |

FOREIGN PATENT DOCUMENTS

| | | |
|---|---|---|
| GB | 2546392 | 7/2017 |
| GB | 2546398 | 7/2017 |
| JP | 2017047244 A | 3/2017 |
| WO | 2009/061915 | 5/2009 |
| WO | 2014151952 A1 | 9/2014 |
| WO | 2016/043845 | 3/2016 |
| WO | 2017/015167 | 1/2017 |
| WO | 2017098266 A1 | 6/2017 |
| WO | 2017098273 A1 | 6/2017 |

OTHER PUBLICATIONS

Search Report issued in corresponding GB Patent Application No. 1709016.8, dated Nov. 22, 2017.
Search Report issued in corresponding GB Patent Application No. 1713625.0, dated Feb. 15, 2018.
Search Report issued in corresponding GB Patent Application No. 1709017.6, dated Nov. 29, 2017.
International Search Report issued in corresponding International Application No. PCT/GB2018/051543, dated Mar. 8, 2018.
Examination Report dated May 24, 2022, for corresponding Australian Patent Application No. 2018280954.
First Office Action dated Feb. 21, 2022, for corresponding Japanese Office Action No. 2019-567231.

* cited by examiner

INSTRUMENT INTERFACE FOR ROBOTIC SURGICAL INSTRUMENT

FIELD

This invention relates to a robotic surgical instrument having an instrument interface comprising a first and second chassis portions attached together.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 to access the surgical site. At its distal end, the instrument comprises an end effector 106 for engaging in a medical procedure.

FIG. 2 illustrates a typical surgical instrument 200 for performing robotic laparascopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. The joints are driven by cables 306, 307 and 308. Pulley 305 is used to direct cables 307 and 308 from their passage over the pitch joint to the yaw joints. Pulley 305 is offset from the central axis of the articulation 203.

In a typical laparoscopy operation, a surgeon utilises many instruments, and hence exchanges one instrument for another many times. It is therefore desirable to minimise the time taken and maximise the ease with which one instrument is detached from a robot arm and a different instrument is attached. Additionally, it is desirable to minimise the time taken in setting up the instrument ready for use once it has been attached to the robot arm.

As such, the surgical instrument 300 may be attached at its proximal end to the distal end of the robotic arm by an instrument interface. The instrument interface may connect, or engage with, an interface of the robotic arm. Mechanical drive to drive the joints of the instrument (e.g. joints 301 and 302) may be transferred to the instrument from the robotic arm via the robotic arm interface and the instrument interface.

SUMMARY

According to the present invention there is provided a robotic surgical instrument, comprising: a shaft; an end effector element; an articulation at a distal end of the shaft for articulating the end effector element, the articulation comprising: a first and second joint permitting the end effector element to adopt a range of configurations relative to a longitudinal axis of the shaft, the first joint being driveable by a first pair of driving elements having a first positional accuracy requirement and the second joint being driveable by a second pair of driving elements having a second positional accuracy requirement lower than the positional accuracy requirement of the first pair of driving elements; and an instrument interface at a proximal end of the shaft, comprising: a chassis formed from the attachment of a first chassis portion to a second chassis portion, the first chassis portion comprising a mounting surface to which the shaft is mounted; wherein the first pair of driving elements are secured relative to the first chassis portion.

The second pair of driving elements may be secured relative to the second chassis portion.

The instrument may further comprise:
a first interface element for driving the first pair of driving elements, the first interface element being fast with the first pair of driving elements so that a displacement of the first interface element with respect to the chassis is transferred to the first pair of driving elements; and
a second interface element for driving the second pair of driving elements, the second interface element being fast with the second pair of driving elements so that a displacement of the second interface element with respect to the chassis is transferred to the second pair of driving elements.

The first and second interface elements may be linearly displaceable through respective maximum displacement ranges, the maximum displacement range of the first interface element being less than the maximum displacement range of the second interface element.

The first interface element may be slideably mounted to the first chassis portion.

The second interface element may be slideably mounted to the second chassis portion.

The instrument interface may further comprise a first set of pulleys about which the first pair of driving elements are constrained to move, the first set of pulleys being rotatably secured to the first chassis portion.

The first set of pulleys may lie on the central plane of the instrument interface containing the longitudinal axis of the shaft.

The instrument interface may further comprise a second set of pulleys about which the second pair of driving elements are constrained to move, the second set of pulleys being rotatably secured to the second chassis portion.

The mounting face may be integrally formed with a distal mounting block portion forming part of the first chassis portion, the distal mounting block portion being mated with a proximal block portion forming part of the second chassis portion.

The mounting surface may be transverse to the longitudinal direction of the shaft.

The first pair of driving elements may lie on a central plane of the instrument interface.

The second pair of driving elements may lie on one side of the central plane of the instrument interface.

The first and second pairs of driving elements may extend between the instrument interface and the articulation though the shaft.

The first joint may permit the end effector element to rotate about a first axis transverse to a longitudinal axis of the shaft.

The second joint may permit the end effector element to rotate about a second axis transverse to the first axis when the instrument is in a straight configuration in which the end effector element is aligned with the shaft.

The surgical instrument may further comprise a second end effector element, and the articulation may comprise a third joint, the third joint being driveable by a third pair of driving elements, the third pair of driving elements being secured relative to the first chassis portion.

The third joint may permit the second end effector element to rotate about the second axis.

The instrument may further comprise a third interface element for driving the third pair of driving elements, the third interface element being fast with the third pair of driving elements so that a displacement of the third interface element with respect to the chassis is transferred to the third pair of driving elements.

The third interface element may be slideably mounted to the first chassis portion.

The instrument interface may further comprise a third set of pulleys about which the third pair of driving elements are constrained to move, the third pair of pulleys being rotatably secured to the first chassis portion.

The third pair of driving elements may have the same positional accuracy requirements as the second pair of driving elements.

The pairs of driving elements may be cables.

BRIEF DESCRIPTION OF DRAWINGS

The present invention will now be described by way of example with reference to the accompanying drawings. In the drawings.

DETAILED DESCRIPTION

The present disclosure is directed to a surgical robotic instrument having an instrument interface at its proximal end comprising a chassis formed from the attachment of two chassis parts. The chassis may be formed of two chassis parts to aid assembly of the instrument interface. The chassis comprises a join along which the two chassis parts mate, or connect. The instrument also comprises a shaft attached to a mounting face of the chassis. The shaft includes at its distal end an end effector element and an articulation for articulating the end effector element relative to the shaft. Driving elements (e.g. cables) extend from the instrument interface through the shaft to the articulation for driving joints of the articulation to thereby articulate the end effector element. Each joint of the articulation is driven by a respective pair of driving elements. The accuracy with which motion of a joint can be controlled is dependent on the positional accuracy of the driving element (i.e., how accurately the driving element's position can be controlled).

One pair of the driving elements may have a higher positional accuracy requirement than the other pair, for example due to the way the driving elements are displaced within the instrument interface, and/or due to the nature of the joint the driving elements drive. The instrument interface is arranged so that one of the chassis portions comprises the whole mounting surface to which the shaft is mounted, and the pair of driving elements having the highest positional accuracy requirement are secured relative to that chassis portion. The pair of driving elements having the lower positional accuracy requirement may be secured relative to the other chassis portion. In other words, the driving element pair having the highest positional accuracy requirement is routed along the chassis part that also includes the mounting surface for the instrument shaft. The position of the mounting surface (and hence shaft) with respect to a pair of driving elements influences the positional accuracy of those driving elements. Securing the driving elements to the same chassis portion that comprises the mounting surface advantageously enables the positional accuracy of the driving elements to be maximised.

Figure 4:
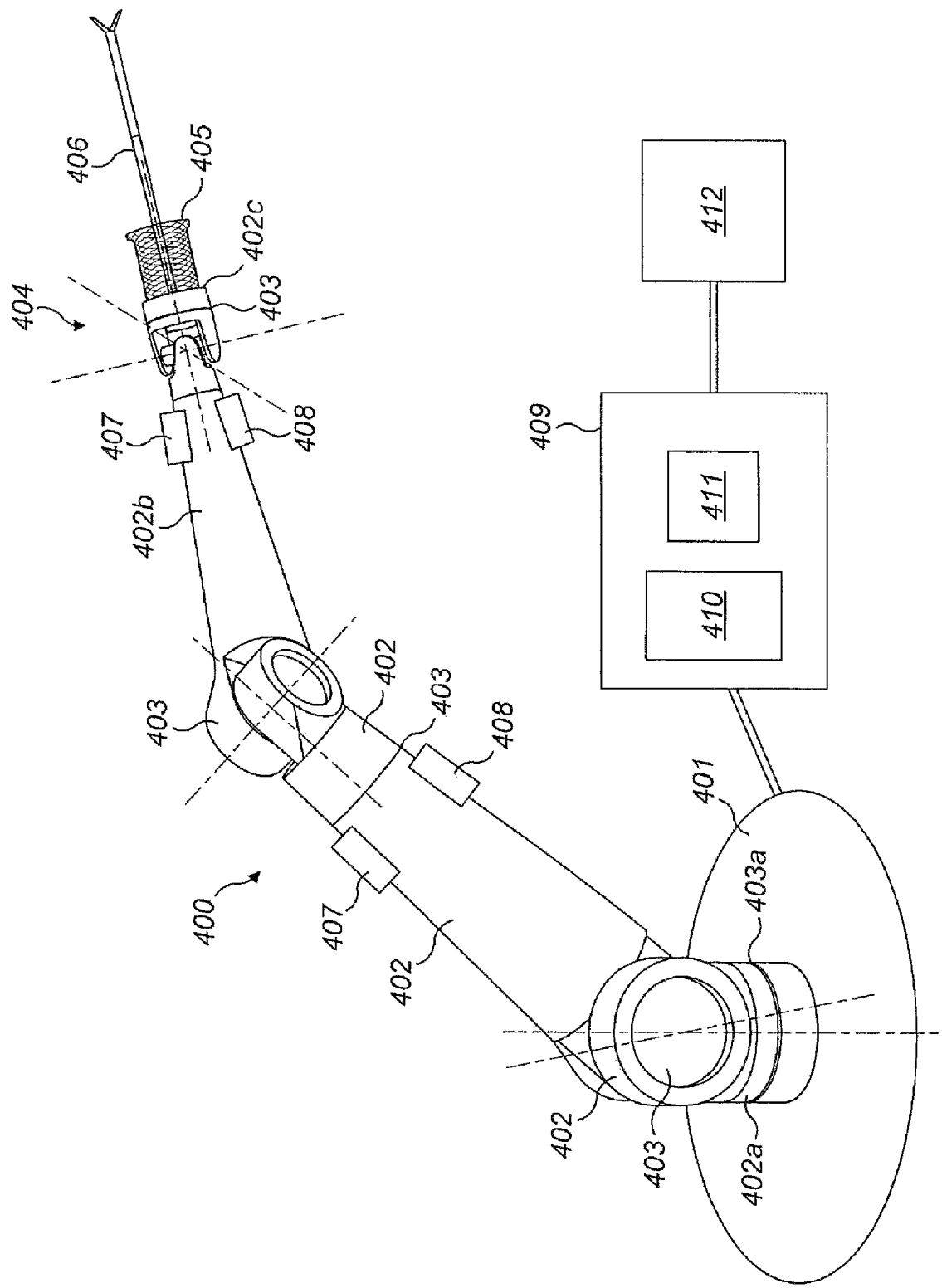
FIG. 4 illustrates a surgical robot.

FIG. 4 illustrates a surgical robot having an arm 400 which extends from a base 401. The arm comprises a number of rigid limbs 402. The limbs are coupled by revolute joints 403. The most proximal limb 402a is coupled to the base by joint 403a. It and the other limbs are coupled in series by further ones of the joints 403. A wrist 404 is made up of four individual revolute joints. The wrist 404 couples one limb (402b) to the most distal limb (402c) of the arm. The most distal limb 402c carries an attachment 405 for a surgical instrument 406. Each joint 403 of the arm has one or more motors 407 which can be operated to cause rotational motion at the respective joint, and one or more position and/or torque sensors 408 which provide information regarding the current configuration and/or load at that joint. The motors may be arranged proximally of the joints whose motion they drive, so as to improve weight distribution. For clarity, only some of the motors and sensors are shown in FIG. 4. The arm may be generally as described in our co-pending patent application PCT/GB2014/053523.

Figure 1:
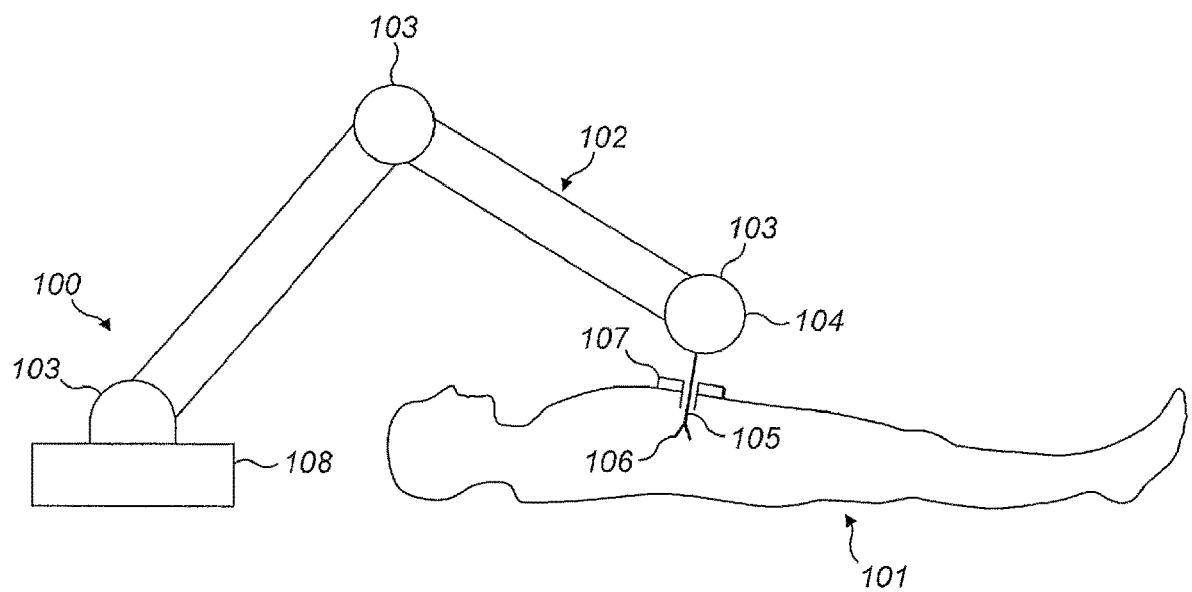
FIG. 1 illustrates a surgical robot performing a surgical procedure.
Figure 2:
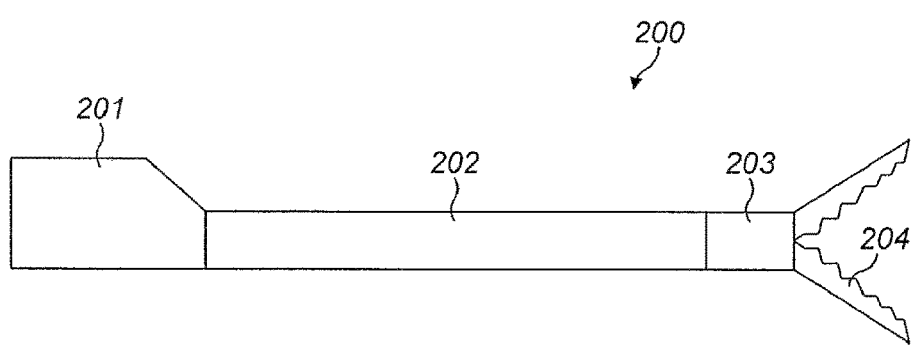
FIG. 2 illustrates a known surgical instrument.
Figure 3:
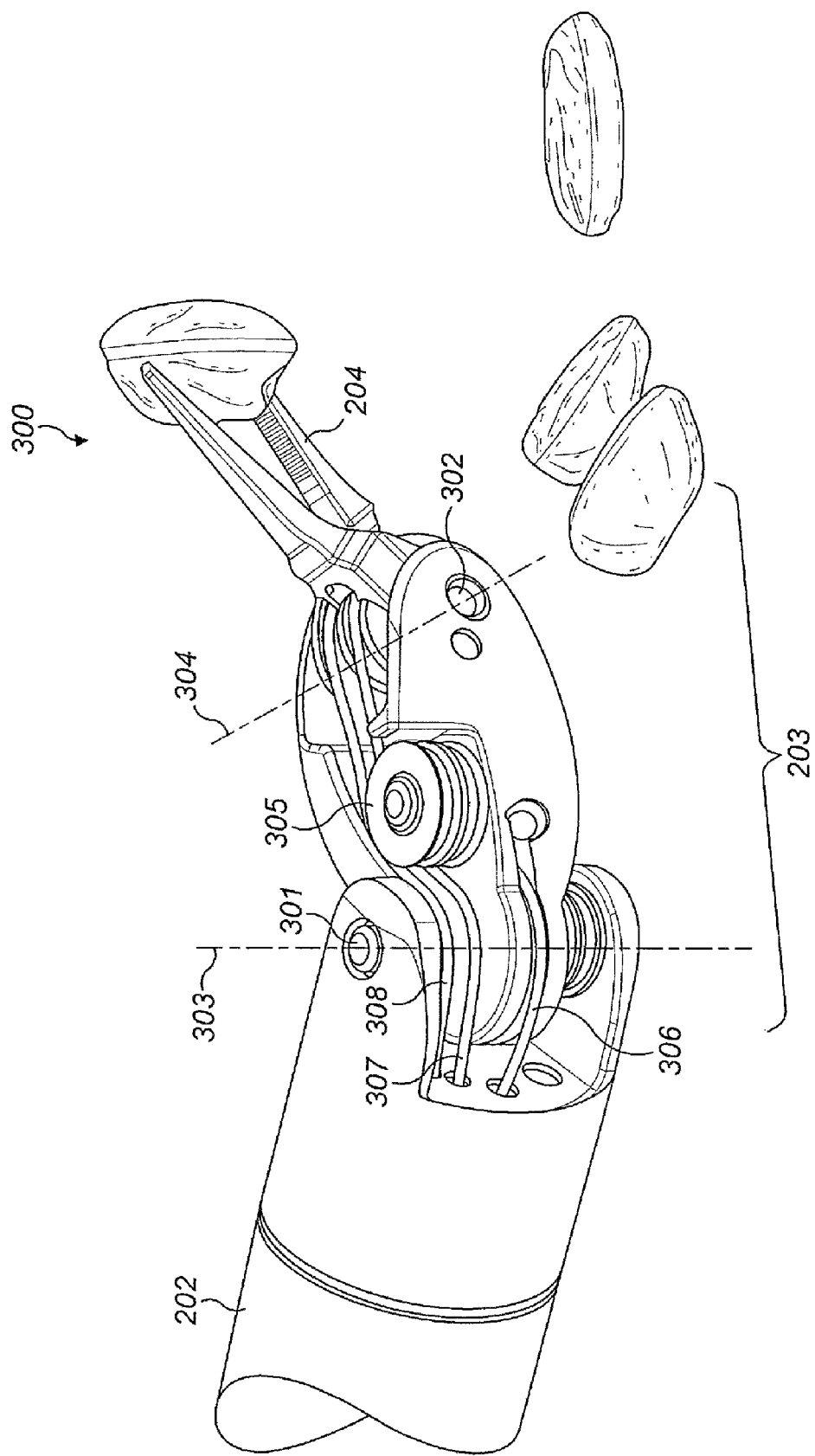
FIG. 3 illustrates a known arrangement of an articulated end effector of a surgical instrument.

The arm terminates in an attachment 405 for interfacing with the instrument 406. The instrument 406 may take the form described with respect to FIG. 2. The attachment 405 comprises a drive assembly for driving articulation of the instrument, and a drive assembly interface for engaging an instrument interface of the instrument 406. Movable interface elements of the drive assembly interface mechanically engage corresponding movable interface elements of the instrument interface in order to transfer drive from the robot arm to the instrument. One instrument may be exchanged for another several times during a typical operation. Thus, the instrument is attachable and detachable from the robot arm during the operation. Features of the drive assembly interface and the instrument interface may aid their alignment when brought into engagement with each other, so as to reduce the accuracy with which they need to be aligned by the user.

The instrument 406 comprises an end effector for performing an operation. The end effector may take any suitable form. The end effector may comprise one or more end effector elements. For example, the end effector elements may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation may comprise one or more joints which permit the end effector to move relative to the shaft of the instrument. The one or more joints in the articulation are actuated by driving elements, such as cables. These driving elements are secured at the other end of the instrument shaft to the interface elements of the instrument interface. The driving elements therefore extend from the instrument interface to the joints of the articulation through the instrument shaft. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 409. A control unit 409 comprises a processor 410 and a memory 411. Memory 411 stores in a non-transient way software that is executable by the processor to control the operation of the motors 407 to cause the arm 400 to operate in the manner described herein. In particular, the software can control the processor 410 to cause the motors (for example via distributed controllers) to drive in dependence on inputs from the sensors 408 and from a surgeon command interface 412. The control unit 409 is coupled to the motors 407 for driving them in accordance with outputs generated by execution of the software. The control unit 409 is coupled to the sensors 408 for receiving sensed input from the sensors, and to the command interface 412 for receiving input from it. The respective couplings may, for example, each be electrical or optical cables, or may be provided by a wireless connection. The command interface 412 comprises one or more input devices whereby a user can request motion of the end effector in a desired way. The input devices could, for example, be manually operable mechanical input devices such as control handles or joysticks, or contactless input devices such as optical gesture sensors. The software stored in memory 411 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 412 can control the instrument 406 to move in such a way as to perform a desired surgical procedure. The control unit 409 and/or the command interface 412 may be remote from the arm 400.

Figures 5A, 5B:
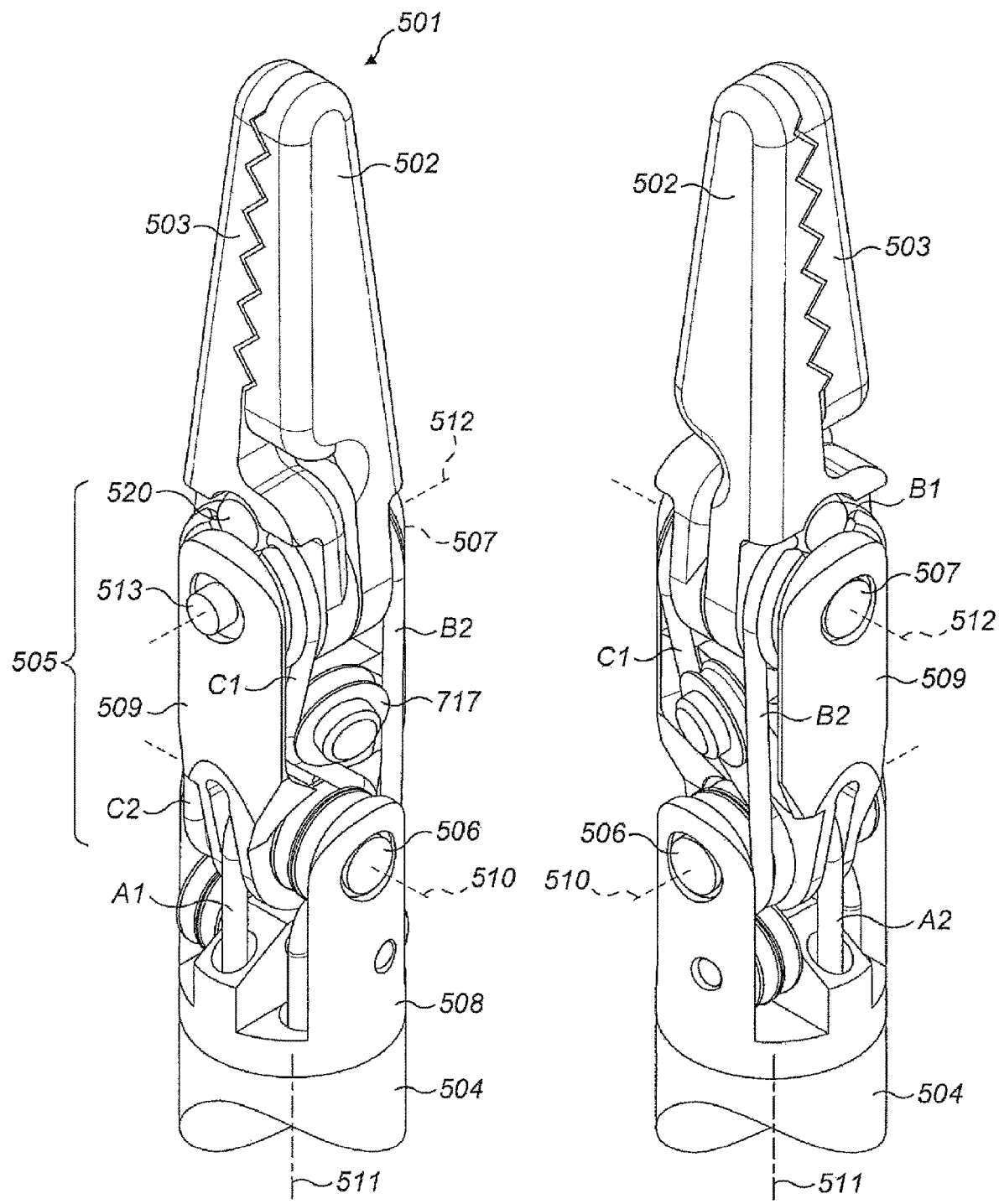
FIGS. 5a and 5b illustrate a distal end of a surgical instrument.

FIGS. 5a and 5b illustrate opposing views of the distal end of an example surgical instrument. In FIGS. 5a and 5b, the end effector 501 comprises a pair of end effector elements 502, 503, which in this example are depicted as a pair of opposing serrated jaws. It will be understood that this is for illustrative purposes only. The end effector may take any suitably form, such as those described above. The end effector 501 is connected to the instrument shaft 504 by articulation 505. Articulation 505 comprises joints which permit the end effector 501 to move relative to the shaft 504. In this example, the articulation 505 comprises three joints. A first joint 506 permits the end effector 501 to rotate about a first axis 510. The first axis 510 is transverse to the longitudinal axis of the shaft 511. The first joint 506 is arranged so that the shaft 504 terminates at its distal end in the joint 506. A second joint 507 permits the first end effector element 502 to rotate about a second axis 512. The second axis 512 is transverse to the first axis 510. A third joint 513 permits the second end effector element 503 to rotate about the second axis 512.

The first end effector element 502 and the second end effector element 503 may be independently rotatable about the second axis 512 by the second and third joints. The end effector elements may be rotated in the same direction or different directions by the second and third joints. The first end effector element 502 may be rotated about the second axis, whilst the second end effector element 503 is not rotated about the second axis. The second end effector element 503 may be rotated about the second axis, whilst the first end effector element 502 is not rotated about the second axis.

FIGS. 5a and 5b depict a straight configuration of the surgical instrument in which the end effector is aligned with the shaft 504. In this orientation, the longitudinal axis of the shaft 511 is coincident with the longitudinal axis of the articulation and the longitudinal axis of the end effector. Articulation of the first, second and third joints enables the end effector to take a range of attitudes (i.e. configurations) relative to the shaft.

The articulation 505 comprises a supporting body 509. At one end, the supporting body 509 is connected to the shaft 504 by the first joint 506. At its other end, the supporting body 509 is connected to the end effector 501 by second joint 507 and third joint 513. Thus, first joint 506 permits the supporting body 509 to rotate relative to the shaft 504 about the first axis 510; and the second joint 507 and third joint 513 permit the end effector elements 502, 503 to rotate relative to the supporting body 509 about the second axis 512.

In the figures, the second joint 507 and third joint 513 both permit rotation about the same axis 512. However, the second and third joints may alternatively permit rotation of the end effector elements about different axes. The axis of rotation of one of the end effector elements may be offset in the longitudinal direction of the shaft 504 from the axis of rotation of the other end effector element. The axis of rotation of one of the end effector elements may be offset in a direction transverse to the longitudinal direction of the shaft 504 from the axis of rotation of the other end effector element. The axis of rotation of one of the end effector elements may not be parallel to the axis of rotation of the other end effector element. The axes of rotation of the end effector elements 502, 503 may be offset in the longitudinal direction of the shaft and/or offset in a direction perpendicular to the longitudinal direction of the shaft and/or angled with respect to each other. This may be desirable as a result of the end effector elements being asymmetric. For example, in an electrosurgical element, a first end effector element may be powered and a second end effector element not powered and insulated from the first end effector element. To aid this, the axes of rotation of the two end effector elements may be offset in the direction perpendicular to the longitudinal direction of the shaft. In another example, a first end effector element may be a blade and a second end effector element a flat cutting surface. To aid use of the blade, the axes of rotation of the two end effector elements may be angled to one another.

The joints of the articulation 505 are driven by driving elements. The driving elements are elongate elements which extend from the joints in the articulation through the shaft 504 to the instrument interface. Each driving element may be capable of being flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements may be inflexible along their main extents. The driving elements may resist compression and tension forces applied along their length. In other words, the driving elements may resist compression and tension forces acting in the direction of their longitudinal axes. The driving elements may have a high modulus. The driving elements may remain taut in operation; they may be not permitted to become slack. Thus, the driving elements are able to transfer drive from the instrument interface to the joints. The driving elements may be cables, for example.

Each joint may be driven by a respective pair of driving elements. Referring to FIGS. 5a and 5b, the first joint 506 is driven by a first pair of driving elements A1,A2. The second joint 507 is driven by a second pair of driving elements B1,B2. The third joint is driven by a third pair of driving elements C1,C2. Each joint of instrument 501 is therefore driven by its own pair of driving elements. In other words, each joint is driven by a dedicated pair of driving elements. The joints may be independently driven. A pair of driving elements may be constructed as a single piece as shown for the third pair of driving elements in FIGS. 5a and 5b. In this case, the single piece is secured to the joint at one point. For example, the third pair of driving elements C1,C2 comprises a ball feature 520 which is secured to the third joint 513. This ensures that when the pair of driving elements is driven, the drive is transferred to motion of the joint about its axis. Alternatively, a pair of driving elements may be constructed as two pieces. In this case, each separate piece is secured to the joint.

The surgical instrument of FIGS. 5a and 5b further comprises a pulley arrangement around which the second and third pairs of driving elements are constrained to move. The pulley arrangement is better illustrated in FIGS. 6a and 6b. The supporting body 509 is not shown in FIGS. 6a and 6b in order to more clearly illustrate the pulley arrangement. The pulley arrangement comprises a first set of pulleys 601. The first set of pulleys 601 is rotatable about the first axis 510. Thus, the first set of pulleys 601 rotate about the same axis as the first joint 506. The pulley arrangement further comprises a second set of pulleys 602. The pulley arrangement further comprises a pair of redirecting pulleys 603, which are described in more detail following the description of the pulley arrangement.

Figure 7:
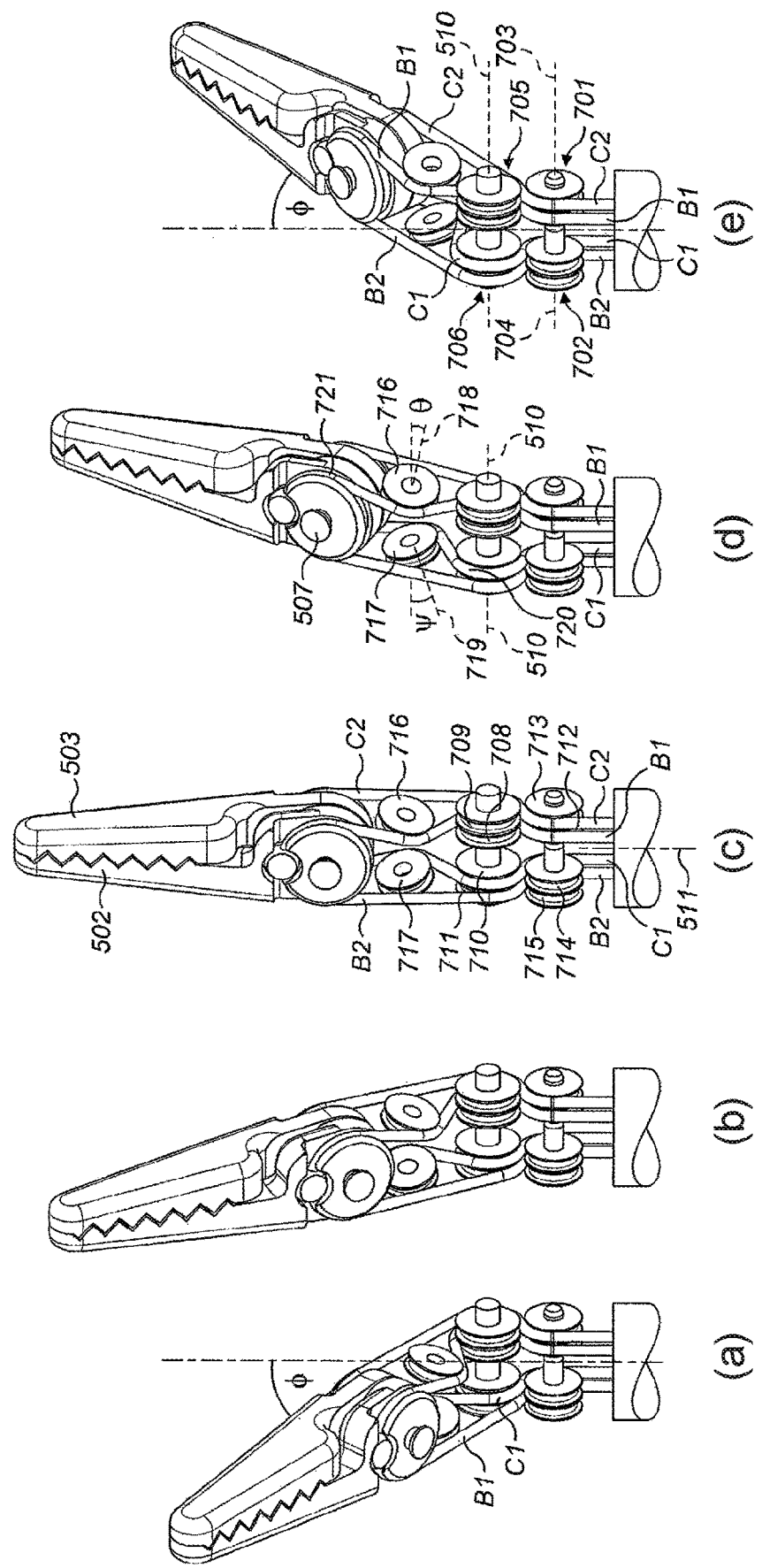
FIG. 7 illustrates a pulley arrangement of the distal end of the surgical instrument of FIGS. 5a and 5b and 6a and 6b in a variety of configurations.

The pulley arrangement is also illustrated in FIG. 7.

The first set of pulleys 601 comprises a first pulley 705 and a second pulley 706. Both the first pulley 705 and the second pulley 706 rotate about the first axis 510. The first pulley 705 and the second pulley 706 of the first set of pulleys are located on opposing sides of the first joint 506 in a longitudinal direction of the shaft 504. The first pulley 705 and the second pulley 06 are located on opposing ends of the first axis 510. The first pulley 705 and the second pulley 706 are located on opposing sides of the first pair of driving elements A1,A2. The first set of pulleys 601 are supported by the arms 530 and 531 of the clevis unit 508. Both the first pulley 705 and the second pulley 706 of the first set of pulleys are rotatably mounted to the clevis unit. Pulley 705 is mounted to the arm 531 and pulley 706 is mounted to the arm 530.

The second set of pulleys comprises a first pulley 701 and a second pulley 702. The first pulley 701 is rotatable about a third axis 703 which is parallel to the first axis 510. The third axis 703 is offset from the first axis 510 both in the longitudinal direction of the shaft and also transverse to the longitudinal direction of the shaft. The second pulley 702 is rotatable about a fourth axis 704 which is parallel to the first axis 510. The fourth axis 704 is offset from the first axis 510 both in the longitudinal direction of the shaft and also transverse to the longitudinal direction of the shaft. The third and fourth axes are parallel but offset from each other. The third and fourth axes are offset from each other in the direction of the rotation axis 512 of the joints 507 and 513. The third axis 703 and fourth axis 704 are in the same plane perpendicular to the longitudinal direction of the shaft 511.

Figure 6A:
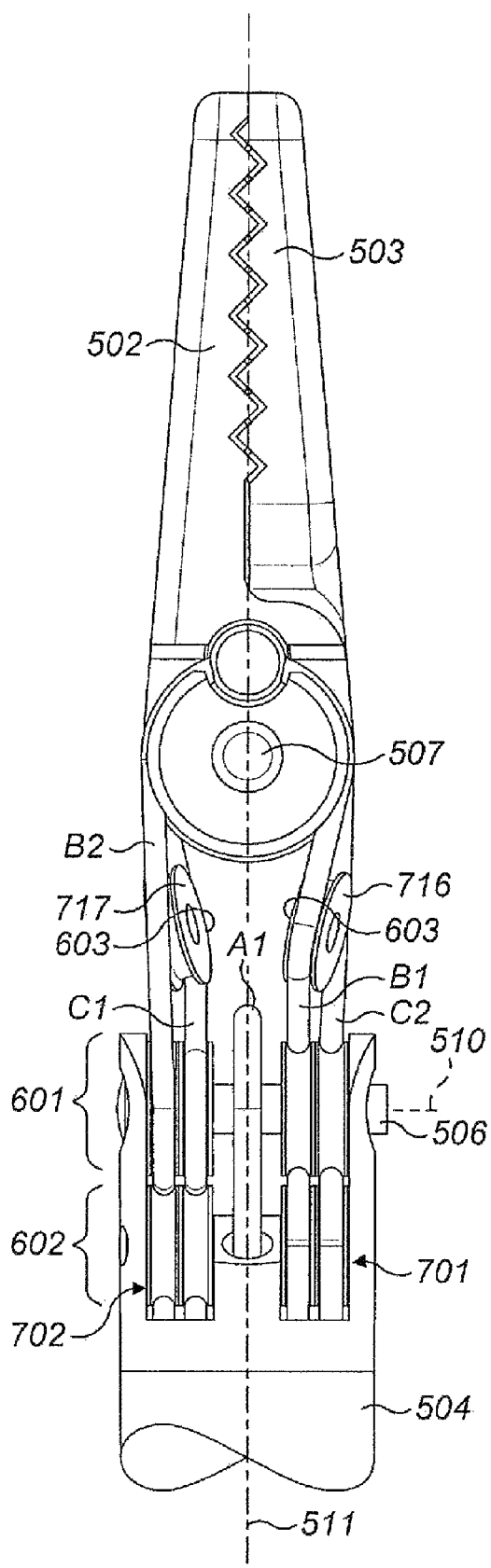
FIGS. 6a and 6b illustrates a further view of the distal end of the surgical instrument.
Figure 6B:
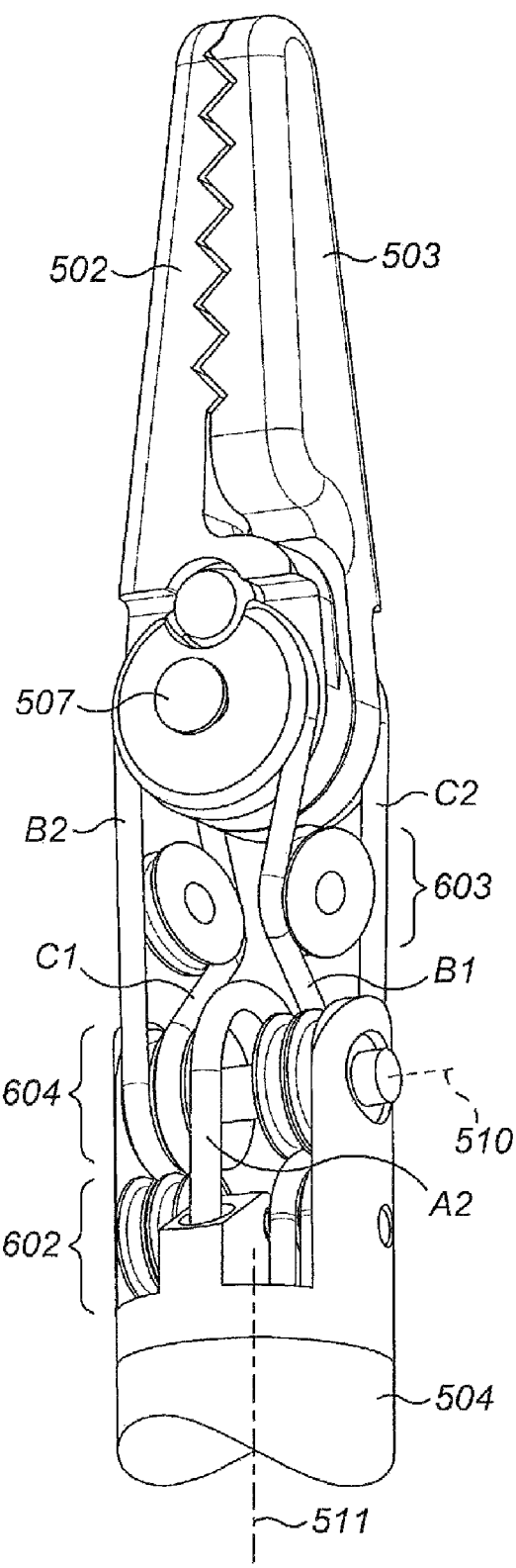

By offsetting the first pulley 701 and the second pulley 702, the driving element wrapped around each pulley is able to extend down the shaft after having wrapped around the pulley. As shown in FIG. 6a, the first pulley 701 and second pulley 702 of the second set of pulleys 602 are located on opposing sides of the first joint 506 in a longitudinal direction of the shaft 504. The first pulley 701 and second pulley 702 are located on opposing sides of the first pair of driving elements A1,A2.

The second set of pulleys is located between the first set of pulleys and the instrument interface end of the shaft. Suitably, the second set of pulleys is located within the shaft as shown in the figures. Thus, the second set of pulleys 602 is proximal of the first set of pulleys 601 along the direction of the longitudinal axis of the shaft 511 (i.e., the first set of pulleys 601 is distal of the second set of pulleys 602). Because both sets of pulleys are supported by the clevis unit 508, it will be understood that the second set of pulleys 602 are proximal of the first set of pulleys independently of the configuration of the instrument and end effector. By locating the second set of pulleys at the distal end of the shaft 508, the distance between the first and second joints is reduced compared to the alternative arrangement in which the second set of pulleys are located in the articulation, thereby reducing the stiffness of the supporting body 509 required to maintain accurate positioning of the end effector 501.

It was mentioned above that the pulley arrangement operates to constrain the motion of the driving elements. In more detail, the second pair of driving elements B1,B2 is constrained to move around opposing sides of the first pulley 705 and the second pulley 706 of the first set of pulleys 601. The second pair of driving elements B1,B2 is constrained to move around opposing sides of the first pulley 701 and the second pulley 702 of the second set of pulleys 601. The second pair of driving elements is constrained to move around opposing sides of the first pulley 705 of the first set of pulleys 601 and the first pulley 701 of the second set of pulleys 602. The second pair of driving elements is constrained to move around opposing sides of the second pulley 706 of the first set of pulleys 601 and the second pulley 702 of the second set of pulleys 602.

The third pair of driving elements C1,C2 is constrained to move around opposing sides of the first pulley 705 and the second pulley 706 of the first set of pulleys 601. The third pair of driving elements C1,C2 is constrained to move around opposing sides of the first pulley 701 and the second pulley 702 of the second set of pulleys 601. The third pair of driving elements is constrained to move around opposing sides of the first pulley 705 of the first set of pulleys 601 and the first pulley 701 of the second set of pulleys 602. The third pair of driving elements is constrained to move around opposing sides of the second pulley 706 of the first set of pulleys 601 and the second pulley 702 of the second set of pulleys 602.

The second and third pairs of driving elements are each constrained to extend over the first joint 506 in order to reach the second and third joints respectively. Thus, the first one of the second pair of driving elements B1 passes over one side of the first pulley 705 of the first set of pulleys on the first joint axis 510, and the second one of the second pair of driving elements B2 passes over an opposing side of the second pulley 706 of the first set of pulleys on the first joint axis 510, so that whatever rotation there is of the supporting body 509 about the first joint 506, the length of the second pair of driving elements B1,B2 is maintained the same. Similarly, the first one of the third pair of driving elements C1 passes over one side of the second pulley 706 of the first set of pulleys on the first joint axis 510, and the second one of the third pair of driving elements C2 passes over an opposing side of the first pulley 705 of the first set of pulleys on the first joint axis 510, so that whatever rotation there is of the supporting body 509 about the first joint 506, the length of the third pair of driving elements C1,C2 is maintained the same. If the arrangement of the instrument interface is symmetric for both the second pair of driving elements B1,B2 and the third pair of driving elements C1,C2, then the length of the second pair of driving elements is the same as the length of the third pair of driving elements for all rotation angles of the supporting body 509 about the first joint 506. In every configuration of the surgical instrument, the second pair of driving elements and the third pair of driving elements remain taut. They are never slack. Thus, there is no backlash when articulating any of the joints of the surgical instrument. Thus, full control of all three degrees of freedom of movement of the surgical instrument is achieved in every configuration of the surgical instrument.

FIG. 7 illustrates the distal end of the surgical instrument in five different configurations. Configuration (c) is the straight configuration previously mentioned, in which the end effector is aligned with the instrument shaft. In configurations (a), (b), (d) and (e), rotation about the first joint has occurred relative to configuration (c). In configurations (a), (b), (d) and (e), no rotation about either the second or third joint has occurred relative to configuration (c). Starting from configuration (c), the driving element A2 (not shown) is pulled in order to cause the rotation about the first axis 510 leading to the arrangement of configuration (b). The driving element A2 is further pulled to cause further rotation about the first axis 510 to lead to the arrangement of configuration (a). Starting from configuration (c), the driving element A1 (not shown) is pulled in order to cause rotation about the first axis 510 in an opposing direction to that in configurations (a) and (b), thereby leading to the arrangement of configuration (d). The driving element A1 is further pulled to cause further rotation about the first axis 510 to lead to the arrangement of configuration (e).

Rotation of the end effector 501 about the first axis 510 is bounded by the maximum travel of the first pair of driving elements A1,A2 about the first joint 506. Configuration (a) shows the end effector 501 at maximum rotation about the first axis 510 in one direction, and configuration (e) shows the end effector 501 at maximum rotation about the first axis 510 in the opposing direction. The maximum rotation angle relative to the longitudinal axis of the shaft 511 in both configurations is the angle cp.

Figure 8:
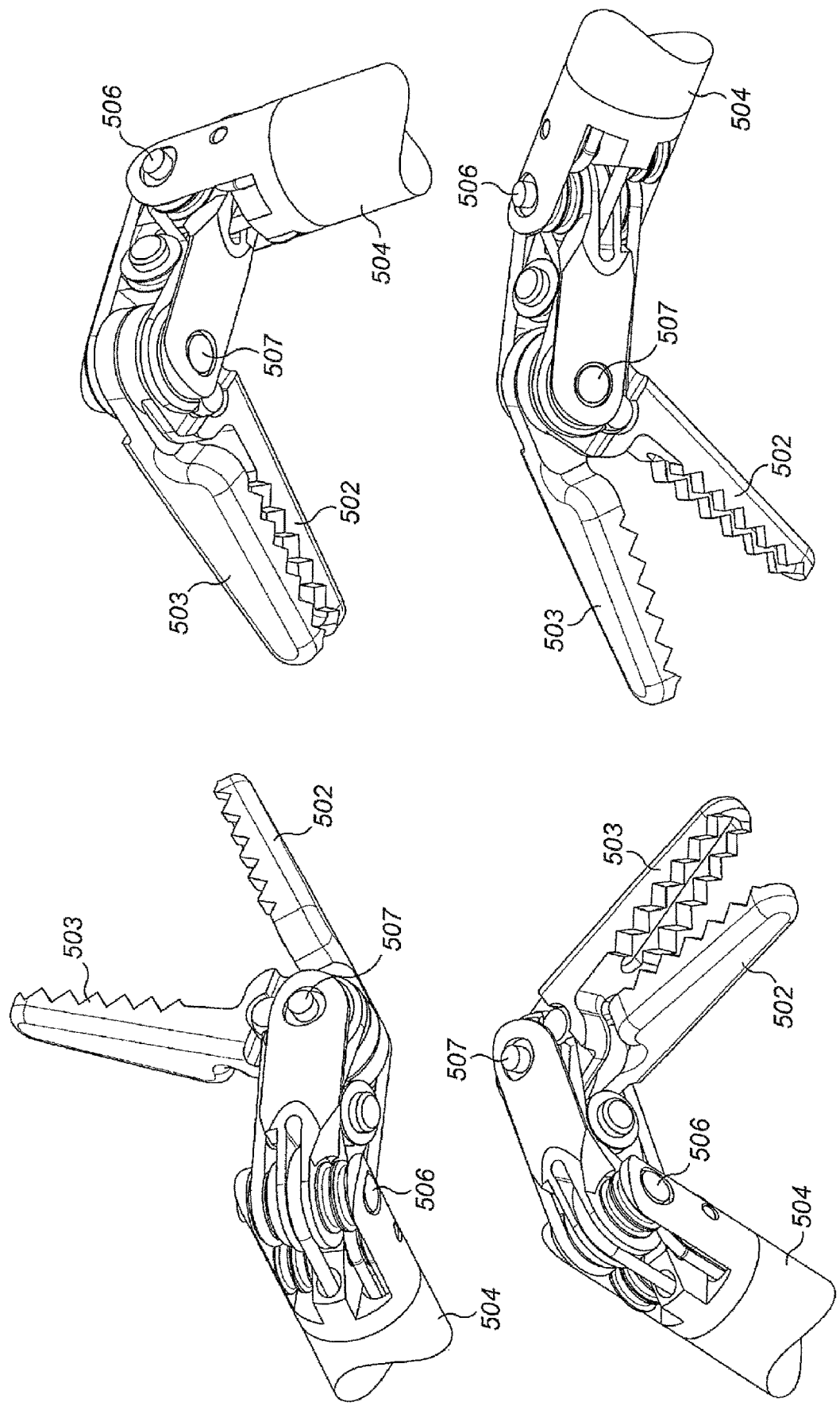
FIG. 8 illustrates the distal end of the surgical instrument in a variety of non-straight configurations.

FIG. 8 illustrates some further configurations of the distal end of the instrument in which articulation about all the first, second and third joints has been driven relative to the straight configuration of FIGS. 5a, 5b, 6a and 6b.

Figure 9:
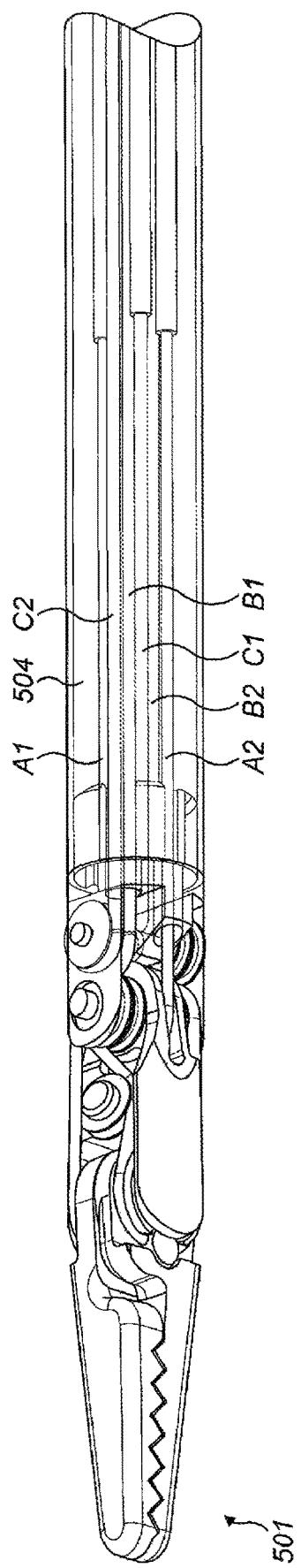
FIG. 9 illustrates arrangements of driving elements in an instrument shaft.

As mentioned above, the first, second and third pairs of driving elements A1,A2, B1,B2, C1,C2 extend through the instrument shaft from the distal end of the shaft 504 connected to the articulation to the proximal end of the shaft connected to a drive mechanism of the instrument interface. FIG. 9 illustrates the three pairs of driving elements extending through the instrument shaft 504.

Figure 10A:
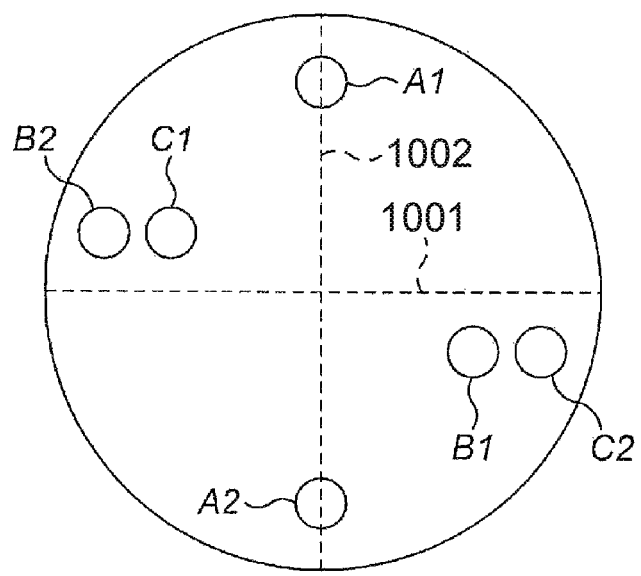
FIGS. 10a and 10b illustrate two cross-sectional views of the instrument shaft showing the position of the driving elements within the shaft.
Figure 10B:
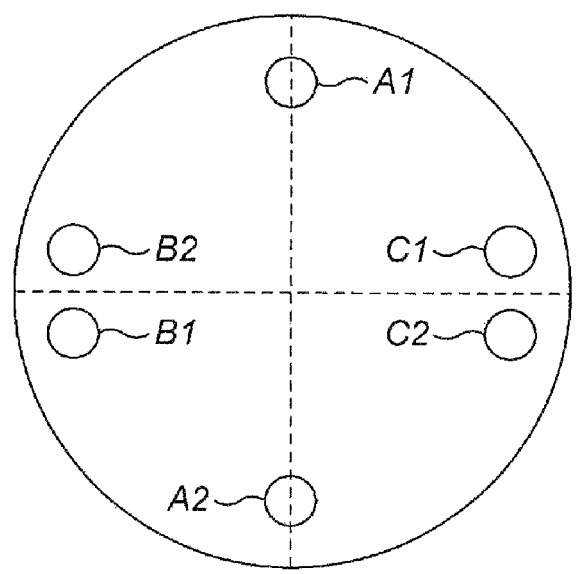

FIGS. 10a and 10b illustrate cross-sections of the shaft depicting the positions of the driving elements.

Configuration (a) of FIG. 10 shows a cross-section of the shaft at the distal end of the shaft. In other words, configuration (a) shows the positions of the driving elements just as they have left the second set of pulleys 602. The driving elements A1 and A2 are at opposing sides of the shaft after having left the first joint 506. The driving elements C1 and B2 are adjacent each other on an opposing side of the shaft to the driving elements B1 and C2 which are also adjacent each other. The driving elements C1 and B2 are offset from the driving elements B1 and C2 about an axis 1001 which is transverse to the axis 1002 connecting driving elements A1 and A2. This is a result of the offset axes of the two pulleys of the second set of pulleys.

Configuration (b) of FIG. 10 shows a cross-section of the shaft at the proximal end of the shaft. In other words, configuration (b) shows the positions of the driving elements as they are about to exit the shaft into the instrument interface. The first pair of driving elements A1 and A2 are on opposing sides of the shaft in a similar arrangement to their arrangement in configuration (a). The first pair of driving elements may be closer together, by virtue of them having moved slightly towards each other over the course of their extent through the shaft. In configuration (b), driving element B1 is located on an opposing side of the shaft to its location in configuration (a). In configuration (b), driving element C1 is located on an opposing side of the shaft to its location in configuration (a). To achieve this, driving element B1 and driving element C1 have not extended down the shaft parallel to the longitudinal axis of the shaft 511. Instead, driving element B1 and driving element C1 have overlapped each other during their extent in the shaft. This overlapping occurs without the driving elements B1 and C1 clashing because of their offset positions in configuration (a) owing to the pulleys of the second set of pulleys 602 having offset axes. Driving element B2 has moved a little in the shaft, but remained on the same side of the shaft as in configuration (a), so as to emerge at the proximal end of the shaft adjacent to driving element B1. Driving element C2 has moved a little in the shaft, but remained on the same side of the shaft as in configuration (a), so as to emerge at the proximal end of the shaft adjacent to driving element C1.

It can be seen from FIGS. 10a and 10b that the first pair of driving elements A1,A2 run parallel to the longitudinal direction of the shaft. Moreover, the first pair of driving elements lie on a central plane of the instrument shaft. The central plane bifurcates the instrument shaft along its length.

Figure 11A:
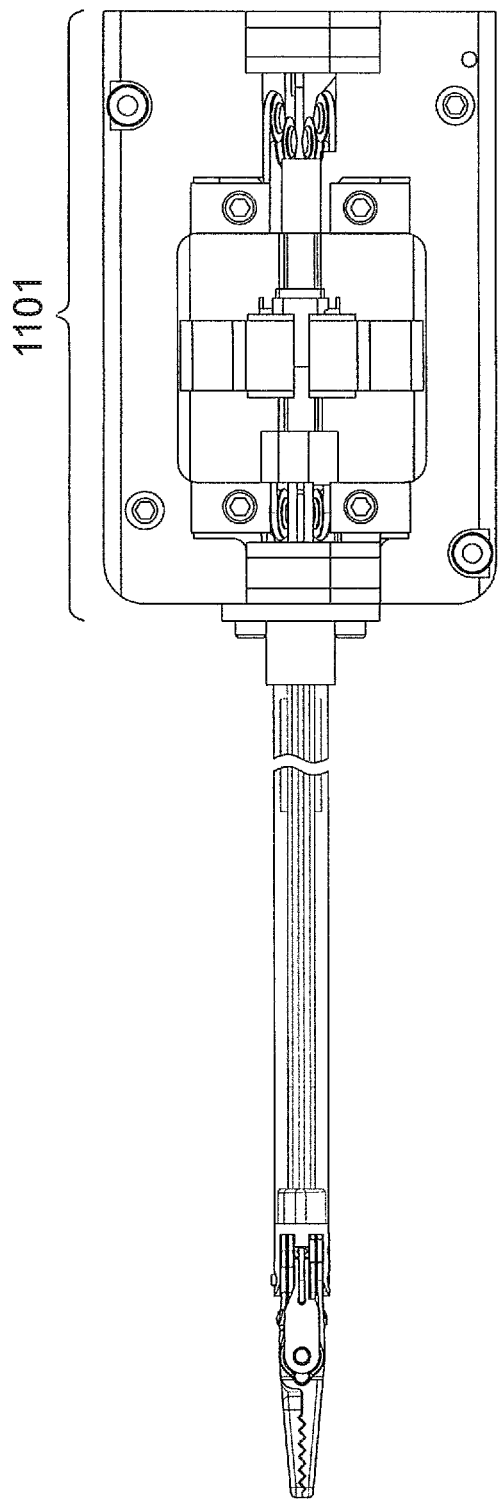
FIGS. 11a and 11b illustrate two views of a surgical instrument including an instrument interface.
Figure 11B:
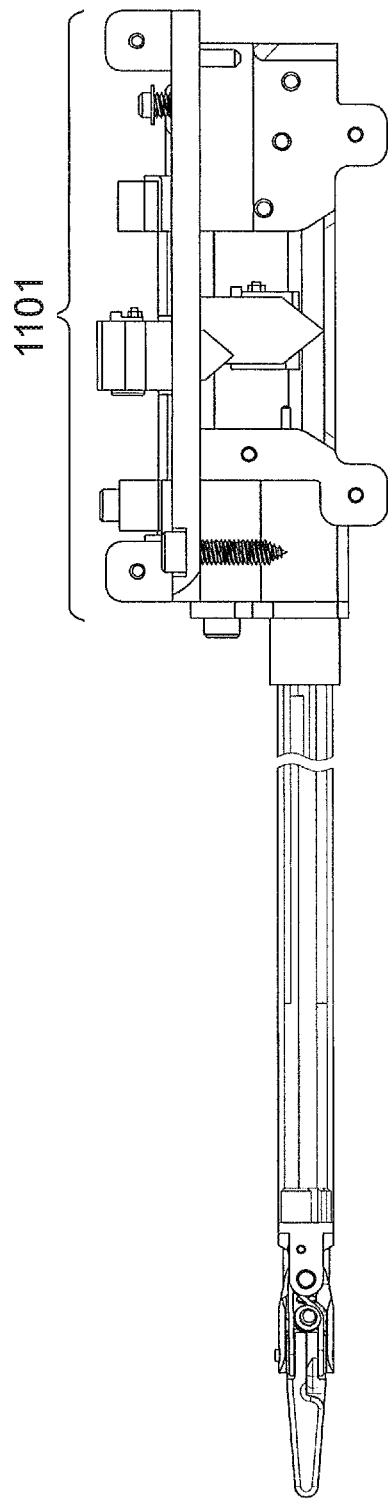

FIGS. 11a and 11b illustrate two views of the first, second and third pairs of driving elements extending from the articulation at the distal end of the instrument shaft to an exemplary instrument interface 1101. Mechanical drive from the robotic arm is transferred to the surgical instrument to articulate the joints of the instrument articulation via the instrument interface 1101 and a drive assembly interface located at the distal end of the robotic arm. To drive a joint of the instrument articulation, an interface element of the drive assembly interface is moved, which moves a mechanically engaged interface element of the instrument interface 1101. Movement of the instrument interface element moves a driving element, which drives a joint of the articulation.

Figure 12A:
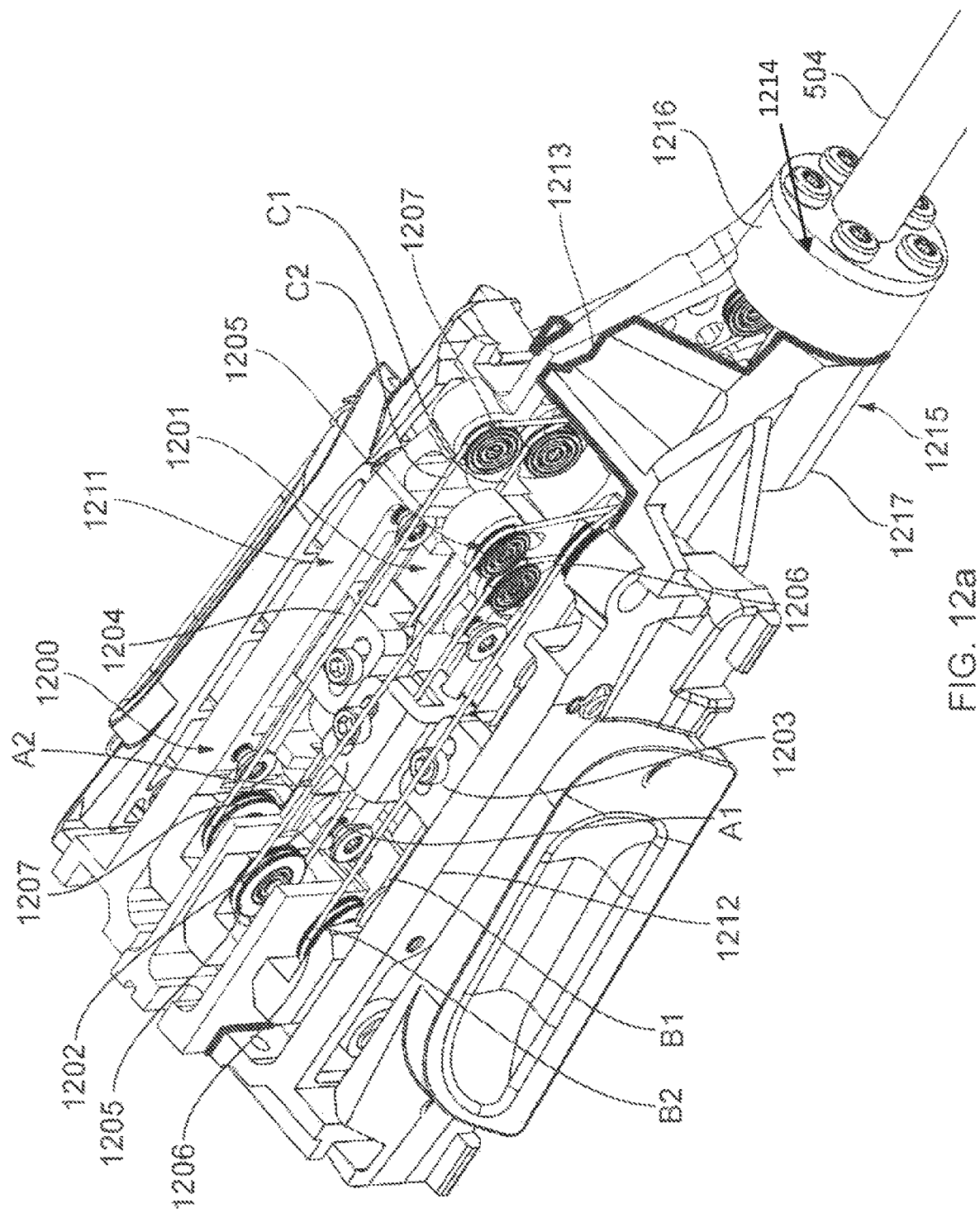
FIG. 12a illustrates a top-side view of the instrument interface.
Figure 12B:
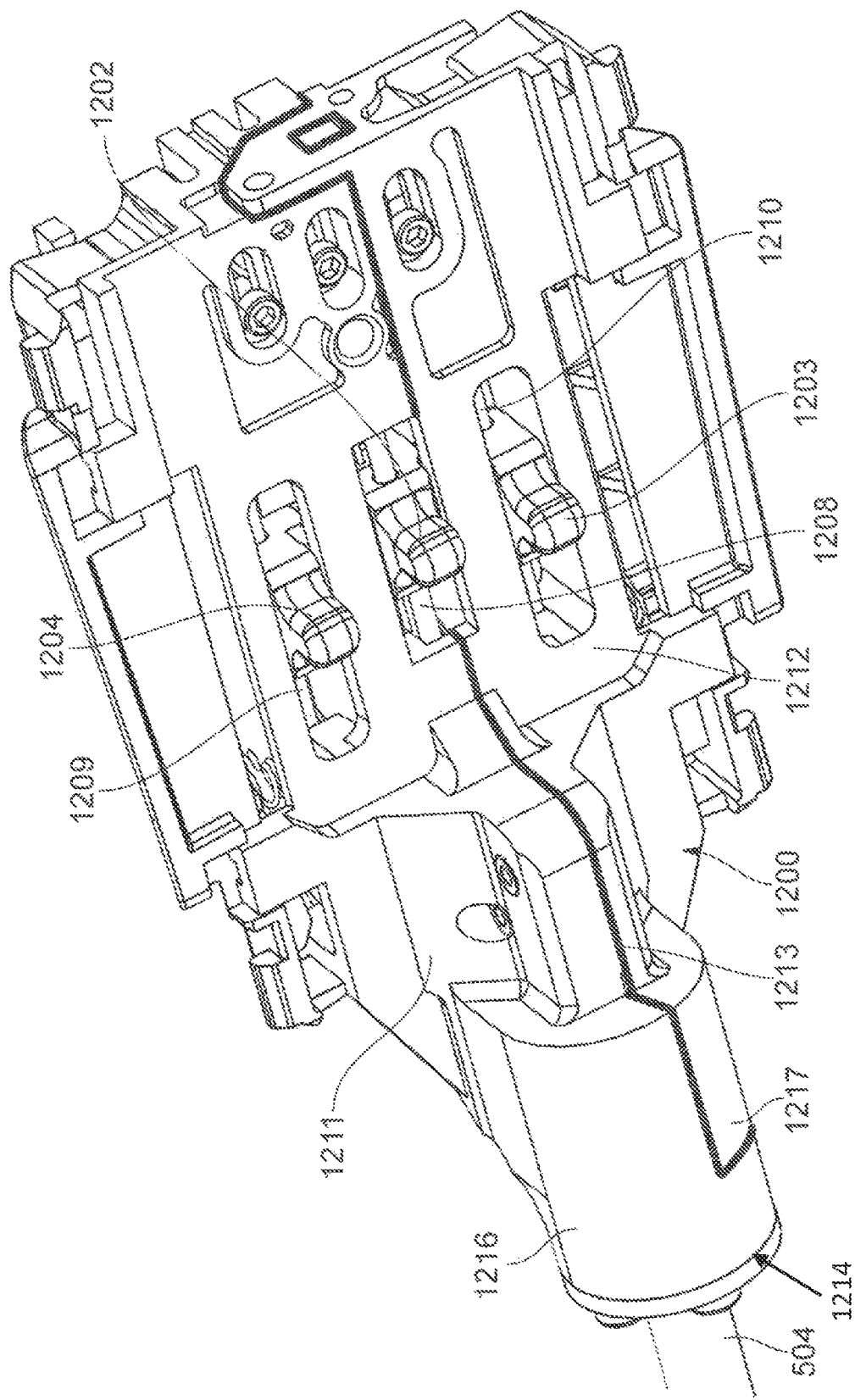
FIG. 12b illustrates an underside-view of the instrument interface.

More detailed views of the instrument interface 1101 are illustrated in FIGS. 12a and 12b. FIG. 12a shows a view of the topside of the instrument interface, and FIG. 12b shows a view of the underside of the instrument interface.

The instrument interface 1101 comprises a chassis 1200 that supports a drive mechanism (denoted generally at 1201) for driving the joints of the instrument articulation. The drive mechanism comprises an arrangement of driving elements and pulleys which transfer drive provided by the robotic arm to the joints, as will be described in more detail below.

The instrument interface comprises three interface elements 1202, 1203 and 1204. The instrument interface elements form part of the instrument interface drive mechanism 1201. The first instrument interface element 1202 engages the first pair of driving elements A1,A2. The second instrument interface element 1203 engages the second pair of driving elements B1,B2. The third instrument interface element 1204 engages the third pair of driving elements C1,C2. Each driving element is secured to its associated instrument interface element. In other words, each driving element is fast with its associated instrument interface element. Each instrument interface element is displaceable relative to the chassis to cause a corresponding displacement of its engaged pair of driving elements.

Thus, in the examples illustrated in FIGS. 12a and 12b, each pair of driving elements engages a single instrument interface element in the instrument interface 1101. Each driving element engages an instrument interface element in the instrument interface. In other words, each driving element engages its own instrument interface element. A single instrument interface element drives a pair of driving elements. Each driving element pair is driven independently by a single instrument interface. In alternative arrangements, there may be a compound driving motion in which more than one instrument interface element drives a single driving element pair, a single instrument interface element drives more than one pair of driving elements, or a plurality of instrument interface elements collectively drive a plurality of driving elements.

The instrument interface elements 1202, 1203 and 1204 are dispersed across the width of the instrument interface. The instrument interface element 1202 is in this example aligned with the longitudinal axis 511 of the shaft 504. The other instrument interface elements 1203 and 1204 are located on either side of the aligned instrument interface element 1202. Specifically, each instrument interface element is constrained to travel along a respective linear path that is parallel to the longitudinal axis of the shaft, and instrument interface elements 1203 and 1204 are located on either side of a plane containing both the longitudinal axis of the shaft and the path of travel of the instrument interface element 1202. The instrument interface elements 1203 and 1204 are therefore not aligned with the longitudinal axis 511 of the shaft 504.

FIG. 12b shows an underside view of the instrument interface 1101. It can be seen that the undersides of the instrument interfaces are in the form of projections. The interface elements may project below the plane defined by the underside of the chassis 1200. Each instrument interface element 1202, 1203, 1204 is receivable in a corresponding socket of a drive assembly interface element. The shapes of the elements and socket may correspond such that when the drive assembly interface element is displaced, this displacement is transferred to the instrument interface element without any slippage. Thus, the body may fit snugly into the socket. The body may fit snugly into the socket at least along a dimension parallel to the displacement direction. In this way, a displacement of the socket causes a corresponding displacement of the body in the displacement direction. The instrument interface element may be displaceable over the same displacement range as its corresponding drive assembly interface element.

The drive mechanism 1201 further comprises sets of pulleys about which each pair of driving elements A1,A2; B1,B2 and C1,C2 are constrained to move within the instrument interface 1101. Specifically, the drive mechanism comprises a first set of pulleys 1205 about which the first pair of driving elements A1,A2 are constrained to move; a second set of pulleys 1206 about which the second pair of driving elements B1,B2 are constrained to move; and a third set of pulleys 1207 about which the third pair of driving elements C1,C2 are constrained to move. Each pulley of these sets of pulleys is supported by the chassis 1200. The pulleys may, for example, be rotatably mounted to the chassis.

The first set of pulleys 1205 lie on a central plane of the instrument interface. This central plane bisects the instrument interface along its longitudinal direction. The first set of pulleys therefore lie on a plane that is parallel to the longitudinal direction of the shaft 504. In the particular arrangement shown in FIG. 12a, the first set of pulleys 1205 lie on a plane that also contains the longitudinal axis 511 of the shaft, i.e. the first set of pulleys 1205 and the longitudinal axis 511 of the shaft are coplanar. It follows that the first set of driving elements A1,A2 lie on the same plane as the pulley set 1205, and thus are also coplanar with the longitudinal axis of the shaft.

The second and third sets of pulleys 1206 and 1207 lie on opposing sides of the central plane containing the first set of pulleys 1205. Thus, neither the second set of pulleys 1206 nor the third set of pulleys 1207 are coplanar with the longitudinal axis 511 of the shaft.

The driving element pairs A1,A2; B1,B2 and C1,C2 extend out of the instrument interface 1101 at its distal end and into the proximal end of the shaft 504, through which they extend up to the joints of the instrument articulation. The chassis of the instrument interface comprises a mounting surface 1214 that the instrument shaft 504 is mounted to. The mounting surface is not directly visible in FIGS. 12a and 12b because it is covered by a congruent flange used to secure the instrument shaft 504. In this example, the mounting surface is an annulus, with the driving element pairs extending through the centre of the annulus. The mounting surface is transverse to the longitudinal direction of the shaft. The mounting surface is planar. The mounting surface encompasses, e.g. encircles, the longitudinal axis of the shaft. The mounting surface forms part of a mounting block 1215 located at the distal end of the chassis. The mounting block in this example has an outer profile that is cylindrical in shape. The mounting block may comprise a bore through which the driving element pairs extend.

Thus, to summarise, the instrument interface 1101 comprises a drive mechanism 1201 to transfer drive from a drive assembly of a robotic arm to the driving element pairs A1,A2; B1,B2 and C1,C2 to thereby drive the joints of the instrument articulation. Within the instrument interface, the pair of driving elements A1,A2 are constrained to move around the set of pulleys 1205 and engage with the first instrument interface element 1202. The pair of driving elements A1, A2 drive rotation of the articulation, and hence the end effector, about the first axis 510 (see FIG. 5a). The pair of driving elements B1, B2 are constrained to move around the set of pulleys 1206 and engage with the second instrument interface 1203. Driving elements B1,B2 drives rotation of the second joint 507. The pair of driving elements C1,C2 are constrained to move around the set of pulleys 1207 and engage with the third instrument interface 1204. Driving elements C1,C2 drives rotation of the third joint 513. Thus, each joint of the instrument articulation is driven by a respective pair of driving elements, and each pair of driving elements is in turn driven by a respective instrument interface element.

Each instrument interface element is displaceable within the instrument interface 1101 to drive its respective pair of driving elements. Since each instrument interface element is fast with a corresponding pair of driving elements, a displacement of the instrument interface element is transferred to a displacement of the pair of driving elements. Each instrument interface element may be displaceable along the same line as the line of the pair of driving elements that it is secured to. Each instrument interface element engages with a corresponding drive assembly interface element of the robot arm. Thus, displacement of the instrument interface element is driven by the robot arm. In this way, the robot arm drives the pairs of driving elements (and hence the joints of the instrument articulation).

In this example, each instrument interface element 1202, 1203 and 1204 is linearly displaceable within the instrument interface 1101. The interface elements may be displaceable along a displacement axis parallel to the longitudinal axis of the shaft 511. Each instrument interface element is mounted to a rail to support, or constrain, or guide, the motion of the interface element within the instrument interface. The rail may therefore be referred to as a guide bar. The rail/guide bar may be linear. As shown most clearly in FIG. 12b, the first instrument interface element 1202 is mounted to rail 1208; the second instrument interface element 1203 is mounted to rail 1209; and the third instrument interface element 1204 is mounted to rail 1210. The interface elements are slideably mounted to the rails to permit relative linear motion between the rail and the interface elements. That is, each interface element 1202, 1203, 1204 is slideable along its respective rail 1208, 1209, 1210. The rails are supported by, and fast with respect to, the chassis 1200. The guide rails may for example be mounted or secured to the chassis. The interface elements are therefore slideable relative to the chassis.

Each instrument interface element can be displaced over a displacement range between a minimum displacement position and a maximum displacement position. The first instrument interface element 1202 is displaceable through a maximum distance of $d_1$. The second interface element 1203 is displaceable through a maximum distance of $d_2$. The third interface element 1204 is displaceable through a maximum distance of $d_3$. In the examples illustrated here, the instrument interface is arranged so that the displacement range of the first instrument interface element 1202 is less than the displacement range of the interface elements 1203 and 1204. That is, $d_1 < d_2$ and $d_1 < d_3$. Here, $d_2 = d_3$. The maximum distance of travel of the second and third interface elements is greater than the maximum distance of travel of the first interface element to counteract parasitic motion of the end effector elements 502 and 503 about axis 512 caused by motion of the joint 506. In more detail, it can be seen from FIGS. 5a,5b and 6a,6b that the driving element pairs B1,B2 and C1,C2 pass around the pitch joint 506. Displacement of driving element 1202, which causes driving element pair A1,A2 to drive joint 506, can therefore cause a displacement of driving element pairs B1,B2 and C1,C2 which drives the joints 507 and 513 resulting in parasitic motion of the end effector elements 502 and 503 about axis 512. Thus, when the end effector elements are rotated about axis 510 of joint 506 (i.e. the end effector elements are in pitch), a greater displacement range of the driving elements B1,B2 and C1,C2 is required to achieve a full working range of motion of the end effector elements about axis 512 compared to when the end effector elements are not rotated about axis 510 (i.e. when the end effector elements are not in pitch). This additional displacement range of the driving element pairs B1,B2, C1,C2 is accommodated by an additional displacement range of the interface elements 1203 and 1204 within the instrument interface, thus making $d_2, d_3 > d_1$.

Thus, the motion of joint 506 is controlled by a shorter range of travel of the instrument interface element than the joints 507 and 513, meaning that greater sensitivity of that motion is preferred. The motion of joint 506 is controlled through movement of the driving elements A1,A2, and thus a greater sensitivity of motion of joint 506 in turn places a greater emphasis on the accuracy of the position of the driving elements A1,A2 compared to the other driving elements B1,B2 and C1,C2. Driving elements A1,A2 may therefore be said to have a higher, or greater, positional accuracy requirement that driving elements B1,B2 and C1,C2.

It has been appreciated that the positional accuracy of the driving element pair A1,A2 can be optimised by a suitable arrangement and assembly of the instrument interface 1101. This will be explained in more detail below.

The chassis 1200 of the instrument interface comprises a first chassis portion 1211 and a second chassis portion 1212. These chassis portions are attached together during assembly to form the chassis. The chassis is formed from the two chassis portions to aid the assembly of the driving elements and pulleys. For example, some of the driving elements and pulleys can be attached to a chassis portion before that portion is attached to the remaining chassis portion to form the chassis. Attaching at least some of the pulleys and driving elements before the chassis portions are combined can enable the driving elements and pulleys to be attached with more ease, particularly those that lie on the central plane of the chassis. In the present example, in which there are three pairs of driving elements and three sets of pulleys to attach, a convenient approach is to attach two sets of driving elements and their associated pulley sets to one of the chassis portions prior to joining the chassis portions together. The remaining pair of driving elements may be attached to the other chassis portion prior to joining the chassis portions, or afterwards.

The two chassis portions are attached together to form the chassis 1200. Each chassis portion is therefore a discrete component part of the chassis, i.e. the two chassis portions are not integrally formed together. As can be seen in FIGS. 12a and 12b, the chassis comprises a join 1213 along which the first chassis portion 1211 mates, or interfaces with, the second chassis portion 1212. Thus, to attach the two chassis portions together, the first chassis portion interfaces the second chassis portion along the join. Securing elements can then be used to secure the two chassis portions together. Thus, each chassis portion may comprise an interfacing surface that engages, or interfaces with the corresponding interfacing surface of the other chassis portion. In other words, the first chassis portion may comprise a first interfacing surface (not shown in FIG. 12), and the second chassis portion may comprise a second interfacing surface (also not shown in FIG. 12). The first interfacing surface interfaces the second interfacing surface to form the chassis 1200. The join 1213 therefore separates the first chassis portion 1211 from the second chassis portion 1212. In this regard, the join 1213 may be said to define the boundary separating the first and second chassis portions.

As shown in FIG. 12b, the join 1213 extends in a generally longitudinal direction of the chassis. The join 1213 may be said to extend along the longitudinal extent of the chassis, though, as shown in the example of FIG. 12b, the join need not be planar.

It can be seen from FIG. 12b that the join 1213 does not extend to the mounting surface 1214 to which the instrument shaft is mounted. That is, the distal-most point of the join is at a location proximal to the mounting surface 1214. The mounting surface 1214 therefore does not contain a join. That is, the entirety of the mounting surface is located on a single side of the join. In other words, the mounting surface is wholly located on a single side of the join. Specifically, the mounting surface (i.e., the entirety of the mounting surface) forms part of the first chassis portion 1211. No part of the mounting surface 1214 forms part of the second chassis portion 1212. Having the entirety of the mounting surface form part of a single chassis portion advantageously enables a stronger and stiffer connection of the instrument shaft to the chassis. It may also enable the instrument shaft to be attached to the chassis with a more accurate axial location.

The join 1213 does however extend into the mounting block 1215 with which the mounting surface is integrally formed. The mounting block 1215 therefore does contain a portion of join 1213. The join 1213 divides the mounting block 1215 into a first block portion 1216 and a second block portion 1217. The first block portion may be referred to as a distal block portion, and the second block portion may be referred to as a proximal block portion. The distal block portion 1216 forms part of the first chassis portion 1211, and the proximal block portion 1217 forms part of the second chassis portion 1212. The mounting surface 1214 is integral with the distal block portion 1216.

The chassis 1200 is arranged so that the first set of driving elements A1,A2 (having the highest positional accuracy requirement) are supported by the same chassis portion 1211 that comprises the mounting surface 1214. That is, the mounting surface 1214 forms part of the first chassis portion 1211, and the first set of driving elements A1,A2 are secured to that first chassis portion. It has been appreciated that the positional accuracy of a driving element pair is dependent on the position of that driving element pair relative to the mounting surface 1214 that supports the instrument shaft, and that the positional accuracy of the driving element pair can be optimised by routing the driving element pair along the chassis portion that comprises the mounting surface. In contrast, it may be more difficult to accurately position a driving element pair that is routed along the chassis portion that does not include the mounting surface.

Thus, the instrument interface is conveniently arranged so that the pair of driving elements having the highest positional accuracy requirement (A1,A2 in this example) are secured relative to the same chassis portion 1211 that includes the mounting surface 1214, and a driving element pair (in this example B1,B2) having a lower positional accuracy requirement are secured relative to the chassis portion 1212 that does not comprise the mounting surface 1214. In other words, the driving element pair B1,B2 are supported by the second chassis portion 1212. This arrangement conveniently optimises the accuracy of the position of the driving elements A1,A2 that drive the joint 506 having the highest desired accuracy of control.

Because in this example the instrument includes three pairs of driving element pairs, the final driving element pair C1,C2 is conveniently arranged to also be supported by the chassis portion 1211. This enables the positional accuracy of two of the driving element pairs to be optimised.

Other components of the drive mechanism 1201 can also be distributed between the first and second chassis portions. For example, the first set of pulleys 1205 about which the first set of driving elements A1,A2 are constrained to move are supported by (e.g. rotatably mounted to) the first chassis portion 1211. Interface element 1202, which engages the driving element pair A1,A2, is also supported by the first chassis portion. For example, the guide bar 1208 on which the interface element is constrained to slide may be mounted to the first chassis portion, thereby making the interface element 1202 slideably mounted to the first chassis portion. Similarly, the pulley set 1207 about which driving element pair C1,C2 are constrained to move are supported by the first chassis portion 1211; and the interface element 1204, which engages the driving element pair C1,C2 is also supported by the first chassis portion. In contrast, the pulley set 1206 about which the driving element pair B1,B2 are constrained to move is supported by (e.g. rotatably mounted to) the second chassis portion 1212 that doesn't comprise the mounting surface. Interface element 1203, which engages the driving element pair B1,B2, is similarly supported by the second chassis portion 1212. For example, the guide bar 1210 on which the interface element is constrained to slide may be mounted to the second chassis portion, thereby making the interface element 1204 slideably mounted to the second chassis portion.

So, by arranging the chassis so that: i) the chassis join connecting the first and second chassis portions does not extend to the mounting surface that supports the instrument shaft (i.e. the mounting surface is not split between the first and second chassis portions); and ii) the driving element pair of the set of driving element pairs having the highest positional accuracy requirement is supported by the same chassis portion that comprises the mounting surface and is not supported by the other chassis portion, the accuracy of the position of the driving element pair can be optimised.

In the examples descried herein, a driving element pair A1,A2 had the highest positional accuracy requirement because its corresponding interface element has a shorter maximum displacement range than the displacement ranges of the other interface elements driving the other driving element pairs B1,B2 and C1,C2. It will be appreciated that the positional accuracy requirements of a driving element pair may in other examples depend on different factors. For example, the positional accuracy requirements may depend on the nature of the joint driven by the driving element pair. The performance criteria of the instrument may for example require certain joints to be controlled with a greater a degree of control and accuracy than other joints. Alternatively, the positional accuracy requirement of the driving element pair may depend on the pulley arrangement by which the driving element pair is constrained to move. For example, more complex pulley arrangements may provide a greater possibility of slippage, meaning it may be desirable to optimise the positional accuracy of the driving element pair where possible to mitigate the loss of accuracy caused by slippage.

In the examples described herein the drive assembly interface included three drive assembly interface elements that transferred drive to three instrument interface elements that transferred drive to three joints of the articulation at the distal end of the instrument shaft. It will be appreciated that the drive assembly interfaces described herein could be modified to include further or fewer drive assembly interface elements to transfer drive to further or fewer instrument interface elements. The instrument interfaces described herein could be modified to include further or fewer instrument interface elements to transfer drive to further or fewer joints of the articulation at the distal end of the instrument shaft. For example, the instrument interface could include two instrument interface elements that drive two driving element pairs only. The driving element pair having the highest positional accuracy requirement can be secured to the same chassis portion that comprises the mounting surface. The other driving element pair (having a lower positional accuracy requirement) may be secured to the same chassis portion or the other chassis portion. The articulation itself could also be modified to include further or fewer joints.

It will also be appreciated that the end effector may only have one end effector element. In this case, the articulation does not include the third joint 513, the instrument interface does not include an instrument interface element for driving the third joint, and the drive assembly does not include a drive assembly interface element for driving that instrument interface element.

The chassis may be formed of more than two chassis portions. In this case, only one of the chassis portions has the features of: i) comprising the entirety of the mounting surface to which the instrument shaft is mounted; and ii) supporting the driving element pair having the greatest positional accuracy requirement.

It will be appreciated that the shape and form of the join between the first and second chassis portions could take many different forms. The join illustrated in FIGS. 12*a* and 12*b* is merely an illustrative example of a join.

The instrument could be used for non-surgical purposes. For example, it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument, comprising:
   a shaft;
   an end effector element;
   an articulation at a distal end of the shaft configured to articulate the end effector element, the articulation comprising:
      a first joint and a second joint permitting the end effector element to adopt a range of configurations relative to a longitudinal axis of the shaft, the first joint being driveable by a first pair of driving elements and the second joint being driveable by a second pair of driving elements; and
   an instrument interface at a proximal end of the shaft, comprising:
      a chassis formed from an attachment of a first chassis portion to a second chassis portion, the first chassis portion comprising a mounting surface to which the shaft is mounted;
   wherein the first pair of driving elements are secured to the first chassis portion and not secured to the second chassis portion, and the second pair of driving elements are secured to the second chassis portion and not secured to the first chassis portion.

2. The robotic surgical instrument as claimed in claim 1, wherein the instrument further comprises:
   a first interface element configured to drive the first pair of driving elements, the first interface element being fast with the first pair of driving elements so that a displacement of the first interface element with respect to the chassis is transferred to the first pair of driving elements; and
   a second interface element configured to drive the second pair of driving elements, the second interface element being fast with the second pair of driving elements so that a displacement of the second interface element with respect to the chassis is transferred to the second pair of driving elements.

3. The robotic surgical instrument as claimed in claim 2, wherein the first and second interface elements are linearly displaceable through respective maximum displacement ranges, the maximum displacement range of the first interface element being less than the maximum displacement range of the second interface element.

4. The robotic surgical instrument as claimed in claim 2, wherein the first interface element is slideably mounted to the first chassis portion.

5. The robotic surgical instrument as claimed in claim 2, wherein the second interface element is slideably mounted to the second chassis portion.

6. The robotic surgical instrument as claimed in claim 1, wherein the instrument interface further comprises a first set of pulleys about which the first pair of driving elements are constrained to move, the first set of pulleys being rotatably secured to the first chassis portion.

7. The robotic surgical instrument as claimed in claim 6, wherein the first set of pulleys lie on a central plane of the instrument interface containing the longitudinal axis of the shaft.

8. The robotic surgical instrument as claimed in claim 6, wherein the instrument interface further comprises a second set of pulleys about which the second pair of driving elements are constrained to move, the second set of pulleys being rotatably secured to the second chassis portion.

9. The robotic surgical instrument as claimed in claim 1, wherein the mounting surface is integrally formed with a distal mounting block portion forming part of the first chassis portion, the distal mounting block portion being mated with a proximal block portion forming part of the second chassis portion.

10. The robotic surgical instrument as claimed in claim 9, wherein the mounting surface is transverse to the longitudinal axis of the shaft.

11. The robotic surgical instrument as claimed in claim 1, wherein the first pair of driving elements lie on a central plane of the instrument interface.

12. The robotic surgical instrument as claimed in claim 1, wherein the second pair of driving elements lie on one side of a central plane of the instrument interface.

13. The robotic surgical instrument as claimed in claim 1, wherein the first and second pairs of driving elements extend between the instrument interface and the articulation though the shaft.

14. The robotic surgical instrument as claimed in claim 1, wherein the first joint permits the end effector element to rotate about a first axis transverse to a longitudinal axis of the shaft, and wherein the second joint permits the end effector element to rotate about a second axis transverse to the first axis when the instrument is in a straight configuration in which the end effector element is aligned with the shaft.

15. The robotic surgical instrument as claimed in claim 1, wherein the surgical instrument further comprises a second end effector element, and the articulation comprises a third joint, the third joint being driveable by a third pair of driving elements, the third pair of driving elements being secured to the first chassis portion, wherein the third joint permits the second end effector element to rotate about a second axis.

16. The robotic surgical instrument as claimed in claim 15, wherein the instrument further comprises a third interface element configured to drive the third pair of driving elements, the third interface element being fast with the third pair of driving elements so that a displacement of the third interface element with respect to the chassis is transferred to the third pair of driving elements.

17. The robotic surgical instrument as claimed in claim 16, wherein the third interface element is slideably mounted to the first chassis portion.

18. The robotic surgical instrument as claimed in claim 15, wherein the instrument interface further comprises a third set of pulleys about which the third pair of driving elements are constrained to move, the third pair of pulleys being rotatably secured to the first chassis portion.

19. The robotic surgical instrument as claimed in claim 15, wherein the third pair of driving elements have the same positional accuracy requirements as the second pair of driving elements.

20. The robotic surgical instrument as claimed in claim 1, wherein the first and second pairs of driving elements are cables.

* * * * *